(12) United States Patent
Vanderspurt et al.

(10) Patent No.: US 7,795,173 B2
(45) Date of Patent: Sep. 14, 2010

(54) LONG-LIVED HIGH VOLUMETRIC ACTIVITY PHOTOCATALYSTS

(75) Inventors: Thomas Henry Vanderspurt, Glastonbury, CT (US); Treese Hugener-Campbell, Coventry, CT (US); Stephen O. Hay, Tolland, CT (US); Timothy N. Obee, South Winsdor, CT (US)

(73) Assignee: Carrier Corporation, Farmington, CT (US)

( * ) Notice: Subject to any disclaimer, the term of this patent is extended or adjusted under 35 U.S.C. 154(b) by 49 days.

(21) Appl. No.: 12/302,639

(22) PCT Filed: May 31, 2007

(86) PCT No.: PCT/US2007/012820

§ 371 (c)(1),
(2), (4) Date: Nov. 26, 2008

(87) PCT Pub. No.: WO2007/143017

PCT Pub. Date: Dec. 13, 2007

(65) Prior Publication Data

US 2009/0239742 A1    Sep. 24, 2009

Related U.S. Application Data

(60) Provisional application No. 60/809,899, filed on Jun. 1, 2006, provisional application No. 60/809,995, filed on Jun. 1, 2006.

(51) Int. Cl.
 *B01J 21/00*    (2006.01)
(52) U.S. Cl. ...................... 502/350; 423/610
(58) Field of Classification Search ................. 502/350; 423/610
See application file for complete search history.

(56) References Cited

U.S. PATENT DOCUMENTS

| | | | |
|---|---|---|---|
| 6,121,191 A | 9/2000 | Komatsu et al. | |
| 6,306,361 B1 * | 10/2001 | Shin et al. | 423/610 |
| 6,685,909 B2 | 2/2004 | Elder et al. | |
| 2002/0050450 A1 | 5/2002 | Newman et al. | |
| 2005/0181937 A1 | 8/2005 | Karvinen et al. | |

OTHER PUBLICATIONS

Official Search Report of the Patent Cooperation Treaty in counterpart foreign Application No. PCT/US07/12820 filed May 31, 2007.
A. Sciafani et al., "Influence of Silver Deposits on the Photocatalytic Activity of Titania", from J Catalysis 168 (1):117-120 (1997).
Z. Zhang et al., "Role of Particle Size in Nanocrystalline TiO2-Based Photocatalysts", from J. Phys. Chem. B 102, 10871-10878 (1998).
S. Mahanty et al., "Effect of Sn Doping on the Structural and Optical Properties of sol-gel TiO", from J. of Crystal Growth 261(1):77-81 (2004).
M. Hirano et al., "Direct Formation of Iron (III)-Doped Titanium Oxide (Anatase) by Thermal Hyd", from J. of the Amer. Ceramic Soc. 87(1):35-41 (2004).

* cited by examiner

*Primary Examiner*—Timothy C Vanoy
*Assistant Examiner*—Michelle Hou
(74) *Attorney, Agent, or Firm*—Cantor Colburn LLP

(57) ABSTRACT

The present disclosure relates to nanocrystalline titanium dioxide ($TiO_2$) photocatalysts having nanocrystallites of less than 14 nanometers in diameter, which are substantially defect-free. The $TiO_2$ photocatalysts form porous particles having a very large mass transfer surface area, large cylindrical pores, and low mass transfer resistance. The nanocrystalline $TiO_2$ photocatalysts provide at least 75% of the photocatalytic activity of commercially-available $TiO_2$ crystals having diameters greater than 20 nm. The nanocrystalline $TiO_2$ photocatalysts may be doped with a metal, metal oxide, or non-metal dopant. A process for preparing the nanocrystalline $TiO_2$ photocatalysts is disclosed. The present disclosure also provides methods for using nanocrystalline $TiO_2$ photocatalysts to remove contaminants.

16 Claims, 8 Drawing Sheets

LONG-LIVED HIGH VOLUMETRIC ACTIVITY PHOTOCATALYSTS

CROSS-REFERENCE TO RELATED APPLICATION(S)

This application claims the benefit of PCT Application No. PCT/US2007/012820 filed May 31, 2007 entitled LONG-LIVED HIGH VOLUMETRIC ACTIVITY PHOTOCATALYSTS, which claims the benefit of U.S. Provisional Application No. 60/809,899, filed Jun. 1, 2006 entitled NANOCRYSTALLINE TITANIUM DIOXIDE ULTRAVIOLET PHOTOCATALYSTS and U.S. Provisional Application No. 60/809,995, filed Jun. 1, 2006 entitled FILTER DEVICES HAVING DEACTIVATION RESISTANT PHOTOCATALYSTS.

BACKGROUND OF THE INVENTION

1. Field of the Invention

The present disclosure relates generally to photocatalysts made of nanocrystallites of titanium dioxide ($TiO_2$). More particularly, the $TiO_2$ nanocrystallites are less than 14 nanometers (nm) in diameter, and treated to minimize the internal defects within the $TiO_2$ nanocrystallites. The present disclosure provides a process for preparing and a method of using such nanocrystalline $TiO_2$ photocatalysts to purify air, water, or other fluids, by photocatalyzing contaminants.

2. Description of the Related Art

Photocatalytic Oxidation (PCO) is a technology used for elimination or reduction of the level of contaminants in fluids such as air or water (or other fluids) using the chemical action of light. When ultraviolet (UV) light is used to energize the photocatalyst, the technology is more specifically termed Ultraviolet Photocatalytic Oxidation (UV-PCO).

Indoor air can include trace amounts of contaminants, including carbon monoxide, ozone, and volatile organic compounds (VOC), such as formaldehyde, toluene, propanal, butene, propionaldehyde and acetaldehyde. Air purifiers using UV-PCO technology can be used to chemically convert these contaminants into less-harmful products, such as carbon dioxide and water, and/or less-polluting products that are more easily removed from the air than their parent compounds.

Other methods have been used to remove contaminants from air. Absorbent air filters, which use absorbent materials such as but not limited to activated carbons, clays, or mesoporous zeolites, remove contaminants from air by trapping the contaminants in the pores of the filter and permitting cleaner air to pass through the filter. An obvious drawback of absorbent filters is that such filters merely block or trap contaminants and the filters are susceptible to clogging, and absorbent air filters often cannot effectively remove certain types of airborne contaminants, such as ozone or carbon monoxide.

Photocatalysts having semiconductor activity have been used in air purification systems for elimination of organic contaminants in air, including titanium dioxide ($TiO_2$), zirconium dioxide ($ZrO_2$), zinc oxide (ZnO), calcium titanate ($CaTiO_3$), tin (stannic) dioxide ($SnO_2$), molybdenum trioxide ($MoO_3$), and the like. Of this group, titanium dioxide ($TiO_2$) is among the most widely-used of the semiconductor photocatalysts because of its chemical stability, relatively low cost, and an electronic band gap that is suitable for photoactivation by UV light.

The drawbacks to $TiO_2$ photocatalysts currently used as air purifiers is the build-up of products of incomplete oxidation, reduction in performance in humid conditions, mass transport issues in high flow-rate systems, inactivation of the $TiO_2$ photocatalyst, and inorganic contamination.

Titanium dioxide ($TiO_2$) is the most stable oxide form of the transition metal titanium. $TiO_2$ is mostly ionic material composed of $Ti^{+4}$ cations and $O^{-2}$ anions. In powder form, $TiO_2$ is white and is widely-used in industry to give whiteness to paint, paper, textiles, inks, plastics, toothpaste, and cosmetics. In crystalline form, $TiO_2$ principally exists as one of three different polymorphic forms: rutile, anatase, and brookite. The two more common polymorphic forms of $TiO_2$, rutile and anatase, have a tetragonal crystal structure, while the less-common brookite form of $TiO_2$ has an orthorhombic crystal structure.

The anatase form of $TiO_2$, which is a low temperature form, has been reported to have the greatest photocatalytic activity of the three polymorphic forms of $TiO_2$ when exposed to UV light. This may be due to a wider optical absorption gap and a smaller electron effective mass in the anatase form that leads to higher mobility of the charge carriers. Anatase is converted to rutile at temperatures above about 600° C., where it is accompanied by crystallite growth and a significant loss of surface area.

The rutile and anatase crystalline structures each have six atoms per unit cell. The anatase form is a body-centered structure and its conventional cell contains two unit cells (i.e., 12 atoms). For both the rutile and anatase forms, titanium atoms are arranged in the crystal structure in such a way that neighboring octahedral units share edges and corners with each other. In the anatase structure, four edges of every octahedral unit are shared edges, as compared within the rutile structure, in which two edges of every octahedral unit are shared edges.

When crystalline $TiO_2$ photocatalyst is irradiated by photons of UV light of less than 387 nm (at room temperature), the band gap energy of $TiO_2$ (3.2 eV) is exceeded, energizing an electron in one of its molecular orbitals to be "promoted" from the valence band into the conduction band of the semiconductor, thereby creating an electron "hole" in the valence band. Electron-hole pairs created in this manner are believed to migrate to the surface where they can initiate redox reactions with contaminants that have adsorbed onto the photocatalyst.

The "promoted" electron eventually recombines with an electron "hole" and returns to the valence band. During the time of electron hole separation, the electron is believed to react with molecular oxygen, and the electron "hole" in the valence band is believed to react with surface hydroxyl groups, forming hydroxyl (.OH) and superoxide radicals, respectively, according to the postulated reactions below:

$$OH^- + h^+(\text{"hole"}) \rightarrow .OH (\text{hydroxyl radical})$$

$$O_2 + e^-(\text{"promoted" electron}) \rightarrow .O_2^{-2}(\text{superoxide radical})$$

One of the most active of currently-available $TiO_2$ photocatalysts, such as DEGUSSA P25 (hereinafter "P25") (Degussa Corporation, Ridgefield Park, N.J., USA) consists of about 80 weight-% of 20 nanometer (nm) anatase $TiO_2$ crystals and about 20 weight-% of larger (about 40 nm) rutile $TiO_2$ crystals. Prepared using a high temperature process, the P25 crystals have a sufficient degree of crystalline perfection to allow sufficient electron hole separation and electron migration to the crystallite surface. The hole at the surface takes the form of a hydroxyl radical (.OH) that is a stronger oxidizing agent than ozone or chlorine. The electron on the surface can form active oxygen species through the reduction of dioxygen, possibly through the formation of superoxide ion, $O_2^-$ and then by its further reduction to peroxide, $O_2^{-2}$. Hydrogen peroxide is formed over photocatalytically active $TiO_2$ in the presence of oxygen and water. Hydrogen peroxide is believed to be the principal agent of remote photocatalytic oxidation (PCO), which describes the oxidation of substances that are very close to, but not in direct physical contact with, photoactive $TiO_2$. The presence of both hydroxyl radicals and an active oxygen species are needed for effective oxidation of formaldehyde to $CO_2$ and $H_2O$ using the anatase form of $TiO_2$.

P25 crystallites having an average crystallite size of about 20 nm and a BET surface area of about 50 $m^2$/gram would seem to be at a theoretical disadvantage as compared with smaller crystallites of $TiO_2$ having an average crystallite size of 10 nm and surface area of greater than 100 $m^2$/g. As used herein, BET (named for the first letters in the surnames of Stephen Brunauer, P. H. Emmett, and Edward Teller, Journal of the American Chemical Society, 1938, vol. 60, pp. 309-319) is a widely-used method in surface science to calculate surface areas of solids by physical adsorption of gas molecules.

Table 1 provides a comparison of average crystallite size with various measures of surface area, including the anatase and rutile forms of $TiO_2$.

TABLE 1

| Average crystallite size, nm | Surface area/ skeletal volume, $m^2/cm^3$ | Available surface area $m^2/cm^3$ | Specific surface area, $m^2$/g anatase | Specific surface area $m^2$/g rutile |
|---|---|---|---|---|
| 5 | 1200 | 800 | 208 | 188 |
| 6 | 1000 | 667 | 174 | 156 |
| 7 | 857 | 571 | 149 | 134 |
| 8 | 750 | 500 | 130 | 117 |
| 9 | 667 | 444 | 116 | 104 |
| 10 | 600 | 400 | 104 | 94 |
| 11 | 545 | 364 | 95 | 85 |
| 12 | 500 | 333 | 87 | 78 |
| 13 | 462 | 308 | 80 | 72 |
| 14 | 429 | 286 | 74 | 67 |
| 15 | 400 | 267 | 69 | 63 |
| 16 | 375 | 250 | 65 | 59 |
| 17 | 353 | 235 | 61 | 55 |
| 18 | 333 | 222 | 58 | 52 |
| 19 | 316 | 211 | 55 | 49 |
| 20 | 300 | 200 | 52 | 47 |
| 21 | 286 | 190 | 50 | 45 |
| 22 | 273 | 182 | 47 | 43 |
| 23 | 261 | 174 | 45 | 41 |
| 24 | 250 | 167 | 43 | 39 |
| 25 | 240 | 160 | 42 | 38 |
| 27 | 222 | 148 | 39 | 35 |
| 29 | 207 | 138 | 36 | 32 |
| 31 | 194 | 129 | 34 | 30 |
| 33 | 182 | 121 | 32 | 28 |
| 35 | 171 | 114 | 30 | 27 |
| 37 | 162 | 108 | 28 | 25 |
| 39 | 154 | 103 | 27 | 24 |
| 40 | 150 | 100 | 26 | 23 |

However, even as Table 1 shows that decreasing average crystallite size of the anatase and rutile forms of $TiO_2$ increases the specific surface area of $TiO_2$, this does not usually result in higher photocatalytic activity, or longer operational life of the photocatalyst, as one would reasonably expect, because heterogeneous catalysis is typically a surface phenomenon. One hypothesis to explain this phenomenon is that the smaller crystallites of $TiO_2$ have imperfections or defects that facilitate rapid electron-hole recombination. See, e.g., Zhang, Z., et al., J. Phys. Chem. B, 1998, vol. 102, pp. 10871-10878, showing that doping anatase $TiO_2$ crystallites with ions such as $Fe^{+3}$ or $Nb^{+5}$ increases the photocatalytic activity. These dopants, located within the crystallites, trap the photon-generated electron, thereby retarding electron hole recombination. This hypothesis is supported by the reported relationship between the amount and nature of the dopant (to improve the activity) and anatase crystallite size.

Another factor in the photocatalytic oxidation activity of $TiO_2$ for destruction of VOCs is increased mass transfer resistance that occurs where there is $TiO_2$ having large surface areas but small pore sizes. The small pores limit the photocatalytic activity sites by inhibiting diffusion of VOCs to the active sites.

In cases where the destruction of VOCs results in the formation of a non-volatile ash, such as the oxidation of a siloxane to $CO_2$, $H_2O$ and $SiO_2$, the ash can block the active site where the VOC was oxidized, and restricts access to other active sites deeper within the catalytic layer.

Thus, currently-available $TiO_2$ photocatalysts have the disadvantage of poor photocatalytic activity by unit weight, lower activity for eliminating contaminants per unit of readily-available surface area, and short life in actual use.

The present disclosure overcomes these drawbacks of previous $TiO_2$ or doped $TiO_2$ photocatalysts.

SUMMARY OF THE INVENTION

The present disclosure provides photocatalysts of nanocrystalline titanium dioxide ($TiO_2$) having nanocrystallites of less than 14 nm in diameter.

The nanocrystalline $TiO_2$ photocatalyst is prepared or treated to minimize internal defects within the $TiO_2$ nanocrystallites. In addition, the aggregate photocatalyst has a pore structure having low mass transfer resistance, making the $TiO_2$ photocatalyst more resistant to deactivation by environmental contaminants, such as siloxane.

The present disclosure also provides $TiO_2$ nanocrystals having at least 75% of the photocatalytic activity of commercially-available $TiO_2$ photocatalysts with larger diameter crystallites, when in the presence of adequate relative humidity in air having sufficient UV radiation.

The present disclosure further provides nanocrystallites of $TiO_2$ that are combined (doped) with one or more metals, metal oxides, non-metals, or other dopants or surface treatments such as tungsten oxide.

The present disclosure still further provides that the nanocrystalline $TiO_2$ photocatalysts can be used in air purifier systems to eliminate contaminants in the air by generating hydroxyl radicals and active oxygen species that oxidize common air contaminants.

The nanocrystalline $TiO_2$ photocatalysts of the present disclosure also can be used as part of siloxane-tolerant photocatalytic air purification systems as well as purification systems for water or other fluids.

DETAILED DESCRIPTION OF THE INVENTION

Figure 1:
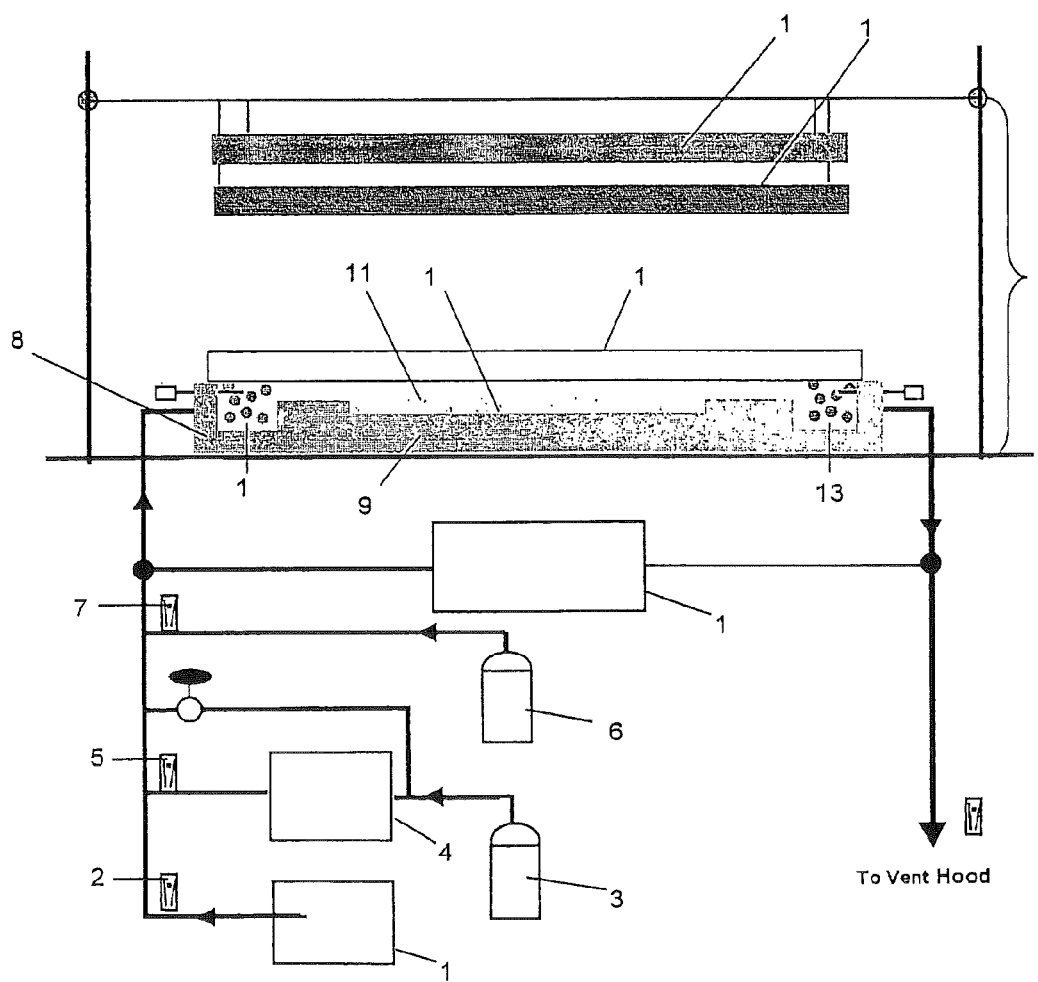
FIG. 1 provides a diagram of a laboratory flat plate intrinsic rate reactor.

The present disclosure provides a photocatalyst made of nanocrystalline titanium dioxide ($TiO_2$) having nanocrystallites of less than 14 nanometers (nm) in diameter. The terms "nanocrystallites" and "crystallites," are used interchangeably in this application, as are their related terms, such as "nanocrystalline" and "crystalline." The nanocrystalline $TiO_2$ photocatalysts form a porous particles with a pore structure that is conducive to low mass transfer resistance, and have ultra-violet (UV) photocatalytic oxidation activity that is resistant to deactivation by environmental contaminants such as siloxane. The nanocrystalline $TiO_2$ photocatalysts may be doped with one or more metals, metal ions, non-metals, or other dopants, or have surface treatments like tungsten oxide.

The $TiO_2$ crystallites are prepared or treated to reduce or minimize internal defects within the $TiO_2$ crystallites. An example of such treatment is the process of annealing the $TiO_2$ crystallite in an oxygen-containing atmosphere, at temperatures above 250° C., and preferably between 350° C. and 450° C., for at least 24 hours. This is sufficient time to reduce internal defects within the $TiO_2$ structure but not so long as to cause large-scale conversion from the anatase form to the rutile form, with the consequent reduction of surface area.

Nanocrystalline $TiO_2$ photocatalysts of the present disclosure are connected through their vertices and/or edges to form pores. The pore structure thus formed is conducive to low mass transfer resistance. The aggregate $TiO_2$ photocatalyst have the majority of the surface area with pores that are 5 nm in diameter or larger. At least 200 meter$^2$ surface area/centimeter$^3$ ($m^2/cm^3$) of skeletal volume of the aggregate photocatalyst has pores that are 6 nm in diameter or larger. The overall distribution of pore size in the aggregate $TiO_2$ photocatalyst has a mode of 10 nm or greater, where mode is used to mean the most frequently occurring number or size in a set. This pore structure results in $TiO_2$ photocatalysts that are resistant to deactivation by environmental contaminants such as siloxane.

The nanocrystalline $TiO_2$ photocatalysts of the present disclosure provide at least 80% of the photocatalytic activity of the photocatalysts that are currently available with larger-diameter $TiO_2$ photocatalysts such as DEGUSSA P25, in an environment having adequate relative humidity in air and in the presence of sufficient UV radiation to activate the $TiO_2$ photocatalyst.

Nanocrystalline $TiO_2$ photocatalysts can be used in air purifier systems to eliminate contaminants in the air, when activated by contact with UV light, by generating hydroxyl radicals and active oxygen species which react with common contaminants, such as VOCs including formaldehyde, toluene, propanal, butene, propionaldehyde and acetaldehyde, to chemically convert contaminants into less-harmful substances, such as water, carbon dioxide, and molecular oxygen, or into other compounds that are more easily removed from the air stream and are less polluting than their parent compounds.

Nanocrystalline $TiO_2$ photocatalysts of the present disclosure can also be used in air purification systems to create photo-induced deodorizing, antibacterial, and self-cleaning effects on air quality. The nanocrystalline $TiO_2$ photocatalysts can be used in air purification systems to convert contaminants in the air to less-harmful compounds.

The nanocrystalline photocatalysts of the present disclosure may also be used for purification of water, and/or other fluids, in the same manner as described for purification of air (or other gases) described herein.

The present disclosure provides nanocrystallites of $TiO_2$ photocatalysts having nanocrystallite sizes of 14 nm or less in diameter that may be combined (doped) with a metal, metal oxide, non-metal, or other dopant. The dopant material can be added to the $TiO_2$ as a coating or layer. In an embodiment of a doped $TiO_2$ photocatalyst of the present disclosure, $TiO_2$ is combined with the doping material as according to the ratio of $Ti_{(1-x)}M_xO_2$, where x is the mole percentage or mole fraction, and M is the doping material. In an embodiment, the mole fraction is less than 0.1. Dopants added to $TiO_2$ photocatalysts of this embodiment can facilitate the elimination of contaminants in various ways, including making the $TiO_2$ photocatalyst more reactive under broader ranges of light (such as visible light), lowering the energy barrier of the contaminant, acting as an oxidation catalyst, facilitating absorbance of the contaminant to the surface of the photocatalyst, and/or rendering the $TiO_2$ photocatalyst less sensitive to the effects of humidity than titanium dioxide photocatalysts used alone.

Metals that can be used as dopants for $TiO_2$ photocatalysts include, but are not limited to, tin, iron, zinc, niobium, tungsten, neodymium, cerium, molybdenum, hafnium, and/or any combinations thereof.

Non-metals that can be used as dopants for $TiO_2$ photocatalysts include, but are not limited to, nitrogen-doped titanium dioxide, or $TiO_{2-x}N_x$.

In addition, the nanocrystalline $TiO_2$ photocatalysts of the present disclosure may have surface treatments, such as tungsten oxide.

Another embodiment of the present disclosure is a photocatalyst made of $TiO_2$ nanocrystallites that are less than 12 nm in diameter. A preferred embodiment has $TiO_2$ nanocrystallites of less than 12 nm in diameter that connected through the vertices or edges to form porous particles of less than 1 micron in diameter, where the majority of the surface area of the porous particles is in pores having diameters of 5 nm or larger. A preferred structure of nanocrystalline $TiO_2$ has at least 200 $m^2$ surface area/cm$^3$ skeletal volume with pores greater than 6 nm in diameter, with the mode of the pore size distribution being 10 nm or greater. A further preferred embodiment has about porous particles with an average pore size greater than 5 nm and diameters that are 10 to 25 times the size of the $TiO_2$ nanocrystallites that make up the particles.

The hydroxyl radical (•OH) that is formed by irradiation of $TiO_2$ photocatalysts by UV light, as described above, is an extremely potent oxidizing agent (having a redox potential of +2.8 eV versus SHE [Standard Hydrogen Electrode]) and is capable of oxidizing nearly all organic compounds. By comparison, redox potentials for conventional oxidants chlorine and ozone are +1.36 eV and +2.07 eV, respectively. When air or water contaminants adsorb onto the UV-activated $TiO_2$ photocatalyst, hydroxyl radicals attack and oxidize the contaminants, and chemically convert the contaminants into water, carbon dioxide, and other substances which are generally less-harmful and/or more easily removed from the air or fluid stream than their parent compounds. Thus, contaminants are chemically converted to less harmful products by this technology, rather than simply trapped and concentrated onto a filter, which leads to more efficient cleaning of air, water, or other fluids.

Electron hole separation, as used herein, is defined as the time between "promotion" of the electron from the valence band to the conduction band, creating an electron "hole" in the valence band, until the electron recombines with an electron hole to return to the valence band. The average time of electron hole separation, also called the lifetime of the charge carrier, is usually about $10^{-9}$ to $10^{-6}$ second.

The valence band may also be called the Highest Occupied Molecular Orbital (HOMO), and the conduction band may also be called the Lowest Unoccupied Molecular Orbital (LUMO). Thus, the promotion of an electron from the valence band to the higher-energy conduction band may also be stated as an electron in a HOMO of $TiO_2$ being energized by light of wavelength less than 387 nm to be "promoted" to a LUMO.

Defects in the internal part of the crystalline $TiO_2$ structure can interfere with electron hole separation, and thereby reduce the photocatalytic activity of nanocrystalline $TiO_2$. Internal defects tend to trap electrons and prevent their passage into the conduction band where the electrons would otherwise be able to interact with oxygen to form peroxide and hydroxyl radicals that can oxidize air contaminants. Internal crystal defects can also shorten the separation time, also reducing photocatalytic activity. By contrast, defects on the outside of a small crystal are expected to improve the photocatalytic activity of nanocrystalline $TiO_2$. As noted above, annealing a nanocrystalline $TiO_2$ photocatalyst can reduce internal crystal defects and thereby improve photocatalytic activity.

Nanocrystalline $TiO_2$ photocatalysts of the present disclosure can be used as part of UV-PCO reactors or air purification systems. Nanocrystalline $TiO_2$ photocatalysts can also be used in UV-PCO reactors which use technologies to prevent or overcome deactivation of the $TiO_2$ photocatalyst. UV-PCO reactors offer the advantages of operating at indoor room temperatures, create a negligible pressure drop, operate with low power consumption, and require little maintenance for a long service life. The nanocrystallites of $TiO_2$ of the present disclosure are sufficiently defect-free to maintain semiconductivity generally associated with $TiO_2$.

When nanocrystalline $TiO_2$ (having a large surface area and large pores) is synthesized using low-temperature synthesis, such as a template-mediated sol gel route, the resulting nanocrystalline material is believed to have a higher concentration of internal crystalline defects as compared with $TiO_2$ that is synthesized using high temperature methods. These internal crystalline defects decrease the photocatalytic activity of the nanocrystalline $TiO_2$. However, the photocatalytic activity of nanocrystalline $TiO_2$ can be increased by calcining the $TiO_2$ photocatalyst in an oxygen-containing atmosphere for a sufficient period of time. Heating $TiO_2$ crystallites under certain conditions causes oxygen to leave the crystal structure, often resulting in increased internal crystalline defects. However, heating the $TiO_2$ crystallites in a clean oxygen environment (for example, an atmosphere free of silicon contaminants), results in a substantially defect-free $TiO_2$ crystallite.

In this process, the $TiO_2$ is preferably calcined for 24 to 72 hours at a calcining temperature that is above 200° C., and more preferably calcined between about 350° C. and 450° C. for the majority of the calcining time. Alternatively, the calcination process may use higher temperatures for shorter periods of time; for example, the calcination steps may use temperatures from about up to 550° C. for 5 hours or less, preferably at temperatures from about 450° C. to about 550° C. for a period of about 3 hours to 5 hours. When calcined for the shorter periods of time, the $TiO_2$ may optionally be further heated for annealing for an additional period of time from about 24 hours to about 72 hours, at temperatures from about 350° C. and 450° C. During this process, the calcination atmosphere should be free of silicon contaminants. If the calcination medium contains water vapor, it should not contact hot silicon-containing refractories.

Referring to the drawings, and, in particular, FIG. 1, there is provided a laboratory flat plate intrinsic rate reactor 8. The reactor 8 has a VOC supply 1 and a VOC mass flow controller 2. The reactor 8 has a nitrogen supply 3 that feeds in to a water bubbler 4, and then to a moist nitrogen mass flow controller 5. Reactor 8 also has an oxygen supply 6 and oxygen mass flow controller 7. Reactor 8 has a machined aluminum block 9, which has a bed 10 for the catalyst-coated slides 11. Reactor 8 has glass beads 12, 13, that serve to mix and distribute gas. The gas atmosphere within the reactor 8 is analyzed by gas analyzer 14. The reactor has an exit gas flow meter 15. Reactor 8 has a first UV A lamp 17 and a second UV A lamp 18. The height of the lamps may be adjusted by the lamp height adjustment 16.

Exemplary embodiments of the nanocrystalline $TiO_2$ having a high surface area and large-pore structure according to the present disclosure were tested and compared for deactivation rates to DEGUSSA P25 $TiO_2$, and the results are provided in the Examples below.

For the Examples, 1 ppm propanal was oxidized by UV-A light at 50% relative humidity (RH), under conditions where about 20% of the propanal was initially oxidized. The deactivation agent was 90 parts per billion (ppb) hexamethyldisiloxane.

Under these conditions, increasing the pore surface area from 18.5 m²/g in P25 (by BJH $N_2$ adsorption) to 77.8 m²/g in Sn-doped $TiO_2$ (designated as UV114 of the present disclosure) decreased the rate of deactivation of the photocatalyst from a loss of 2.05% per hour (for P25) to a loss of 0.335% per hour for UV114, as compared with their respective initial photocatalytic activities.

Thus, assuming that the photocatalytic deactivation rate is proportional to the siloxane concentration, the activity of P25, in the presence of 90 ppb hexamethyldisiloxane, would be expected to drop to 50% of its initial activity in about 24 hours. Extrapolating these results to a smaller concentration of the deactivating agent, 1 ppb hexamethyldisiloxane, the photocatalytic activity of P25 would be expected to drop to 50% of its initial activity in 90 days. By comparison, the photocatalytic activity of UV 114 would be expected to drop to 50% of its initial activity after 550 days in the presence of 1 ppb of hexamethylsiloxane.

Example 1

In this example, the conventional BET-specific surface area measurement units of m²/g are used for convenience. 1" by 3" slides were coated with an aqueous suspension of nanocrystalline $TiO_2$, and allowed to dry. The $TiO_2$ coating was sufficient to absorb 100% of the incident light when used in the intrinsic rate reactor according to FIG. 1. This reactor is a flat plate photocatalytic reactor having UV illumination that is provided by two black-light lamps (SpectroLine XX-15A). The spectral distribution was symmetrical about a peak intensity located at about 352 nm and extending from 300 nm to 400 nm. The illumination intensity was varied by adjusting the distance between the lamp and the titania-coated glassplate. UV intensity at the reactor surface was measured by a UVA power meter. High-purity nitrogen gas passed through a water bubbler to set the desired humidity level. The contaminants were generated either from a compressed gas cylinder, such as Propanal/$N_2$, or from a temperature controlled bubbler. An oxygen gas flow was then combined with the nitrogen and contaminant flows to produce the desired carrier gas mixture (15% oxygen, 85% nitrogen).

The titania-coated aluminum 1"×3" slides were placed in a well, measuring 1" by 18" that was milled from an aluminum block. The well was then covered by a quartz window that was 96% UVA transparent. Gaskets between the quartz window and aluminum block created a flow passage above the titania-coated glass plates. The flow passage had a 1" width and a 2 mm height.

Contaminated gas entered the reactor by first passing through a bed of glass mixing beads. Next, the gas flow entered a 1" by 2 mm entrance region of sufficient length (3") to produce a fully-developed laminar velocity profile. The gas flow then passed over the surface of the titania-coated glass plates. Finally, the gas passed through a 1" by 2 mm exit region (3" long) and the second bed of glass beads before exiting the reactor.

Figure 2:
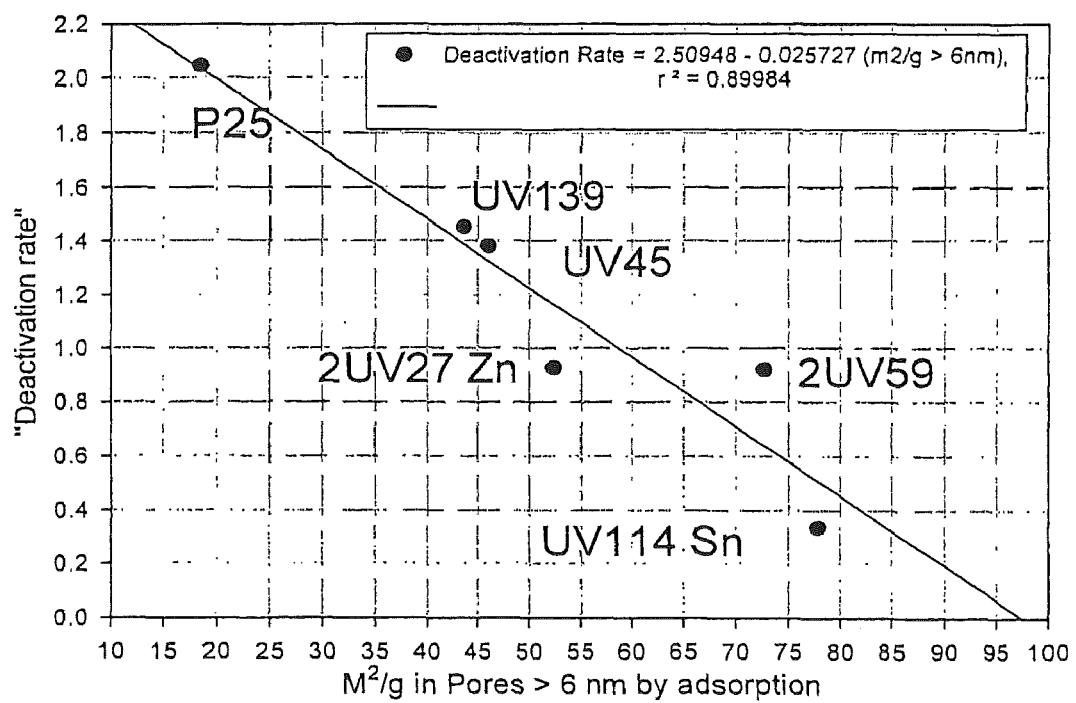
FIG. 2 illustrates the longevity of various $TiO_2$-based photocatalysts in the presence of 90 parts per billion (ppb) hexamethyldisiloxane.

Referring now to FIG. 2, the longevity of various $TiO_2$-based photocatalysts was determined in the presence of 90 ppb hexamethyldisiloxane, using the intrinsic rate reactor of FIG. 1. The deactivation rate of the photocatalyst was determined by the slope of a straight line that represents the catalyst performance during its initial stages of operation. The value for P25 represents the average of several tests.

As shown by data in Table 2 below, and as shown graphically in FIG. 2, the rate of photocatalytic activity loss, expressed in % initial activity per hour, decreases as the surface area in pores greater than or equal to 6 nm becomes larger. However, this linear relationship does not hold with the total BET surface area, or the surface area in pores greater than 4 nm in diameter, as determined by $N_2$ adsorption and BJH analysis of this adsorption as performed by a Micrometrics ASAP 2010 surface area determination unit.

TABLE 2

| Catalyst | Rate of activity loss, % initial activity/hr | BET | BET APD | SA ≧ 4 nm | SA ≧ 5 nm | SA ≧ 6 nm |
|---|---|---|---|---|---|---|
| P25 | −2.04 | 52.0 | 8.8 | 25.5 | 20.7 | 18.5 |
| UV139 | −1.45 | 66.6 | 8.9 | 59.2 | 49.8 | 43.5 |
| UV45 | −1.38 | 64.6 | 22.0 | 50.8 | 47.6 | 46.0 |
| 2UV27 | −0.93 | 123.1 | 7.2 | 101.2 | 71.7 | 52.3 |
| 2UV59 | −0.92 | 82.5 | 21.4 | 76.3 | 74.5 | 72.7 |
| UV114 | −0.33 | 99.4 | 21.4 | 85.0 | 80.3 | 77.8 |

Figure 3:
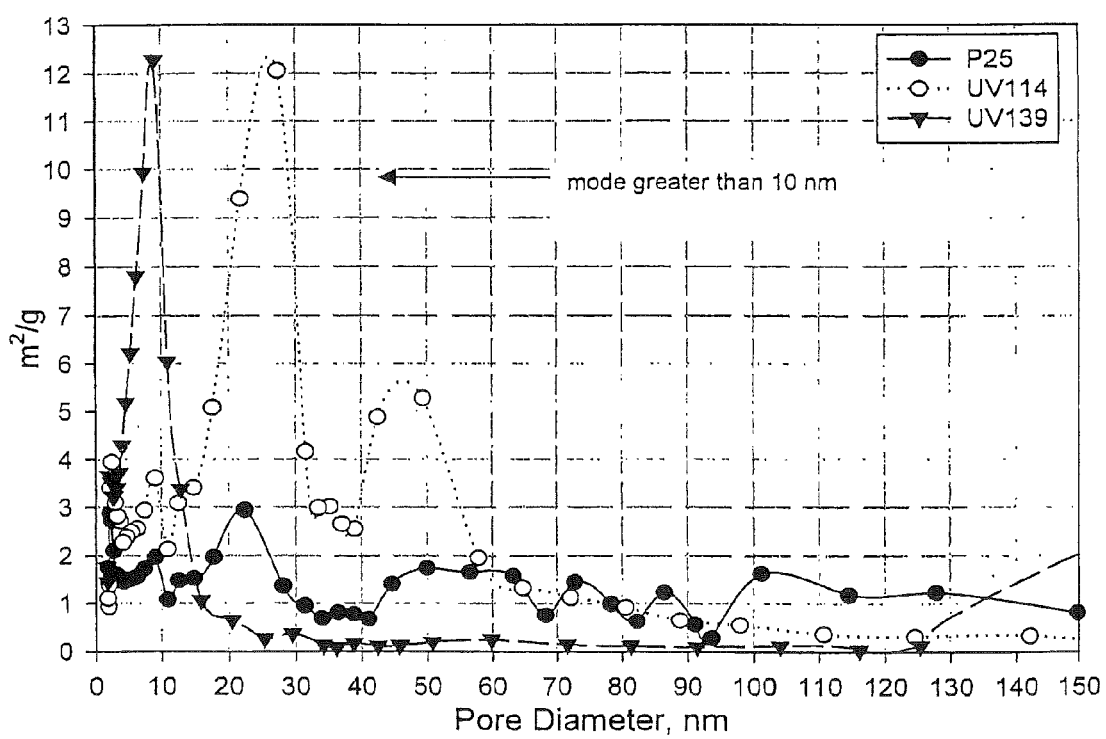
FIG. 3 illustrates the distribution profile of pore sizes for photocatalysts of the present disclosure as compared with other photocatalysts.

Referring now to FIG. 3, the distribution of pore sizes for photocatalysts P25, UV139, and UV114 are shown as the relation of Pore Diameter (X-axis) and Specific Surface Area (Y-axis). When the data of Table 2 is considered in light of the pore size distribution data in FIG. 3, the photocatalysts with the lowest deactivation rates not only possess increased surface area in pores of greater than 6 nm, but also the mode (i.e., most prevalent) pore size is about 10 nm or greater, and may be bimodal, as shown by the graph of pore size for UV114.

The data in Table 2 shows that UV114, which has 4.2 times the surface area in pores greater than 6 nm as compared with P25, has a projected life that is at least 6 times longer than P25 when challenged by hexamethyldisiloxane at a concentration of 90 ppb, under the same UV illumination. Extrapolating these data to a time-averaged concentration of 2 ppb of siloxanes, and assuming that the deactivation rate is linear with respect to concentration of contaminants, UV114 should retain at least 20% of its initial activity after 10,000 hours, while P25 would be projected to lose 80% of its initial activity after only 1,700 hours, under the same challenge of siloxanes.

Figure 4:
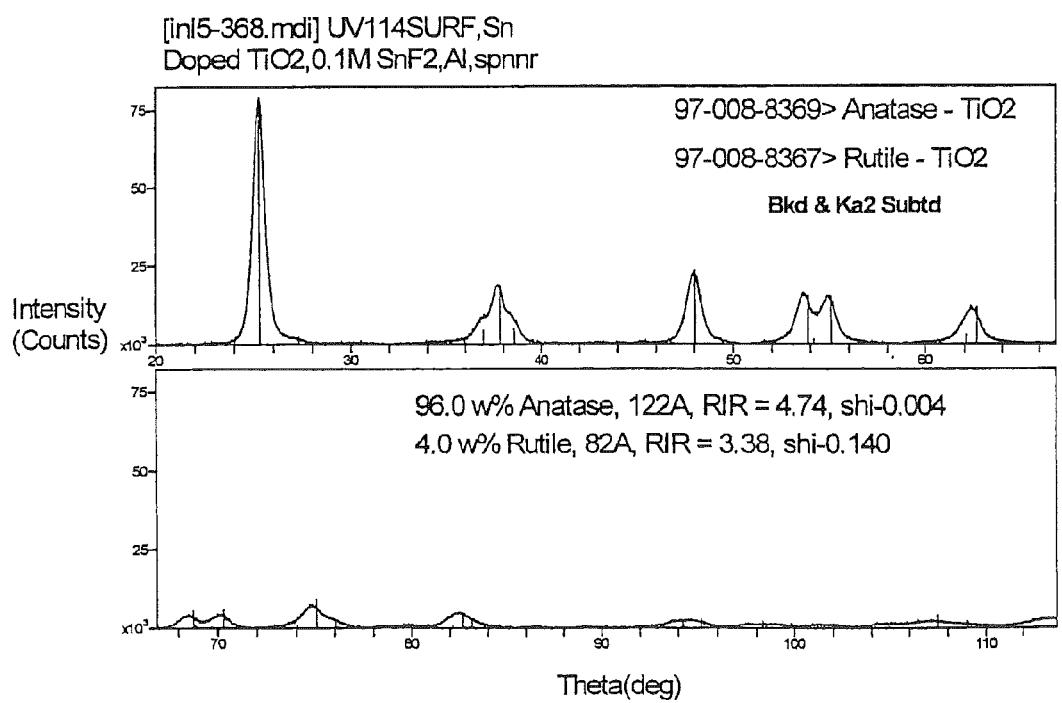
FIG. 4 illustrates a powder X-ray diffraction pattern of a $TiO_2$ photocatalyst of the present disclosure, UV114, having anatase crystallites of 122 Angstroms (12 nm).

FIG. 4 illustrates a powder x-ray diffraction pattern of a photocatalyst of the present disclosure, UV114 Sn, which is predominantly anatase and has crystallites of about 12 nm (122 Angstroms) in diameter.

Figure 5:
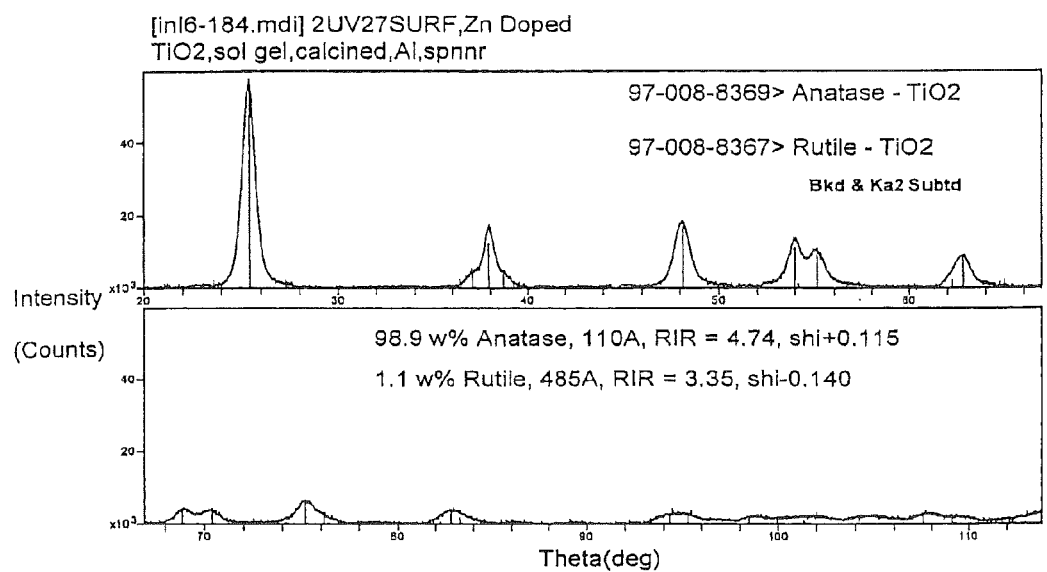
FIG. 5 illustrates a powder X-ray diffraction pattern of a $TiO_2$ photocatalyst of the present disclosure, 2UV27, having anatase crystallites of 110 Angstroms (11 nm).

FIG. 5 illustrates a powder x-ray diffraction pattern of a photocatalyst of the present disclosure, 2UV27, which is also predominantly anatase and has crystallites of about 11 nm (110 Angstroms) in diameter.

Figure 6:
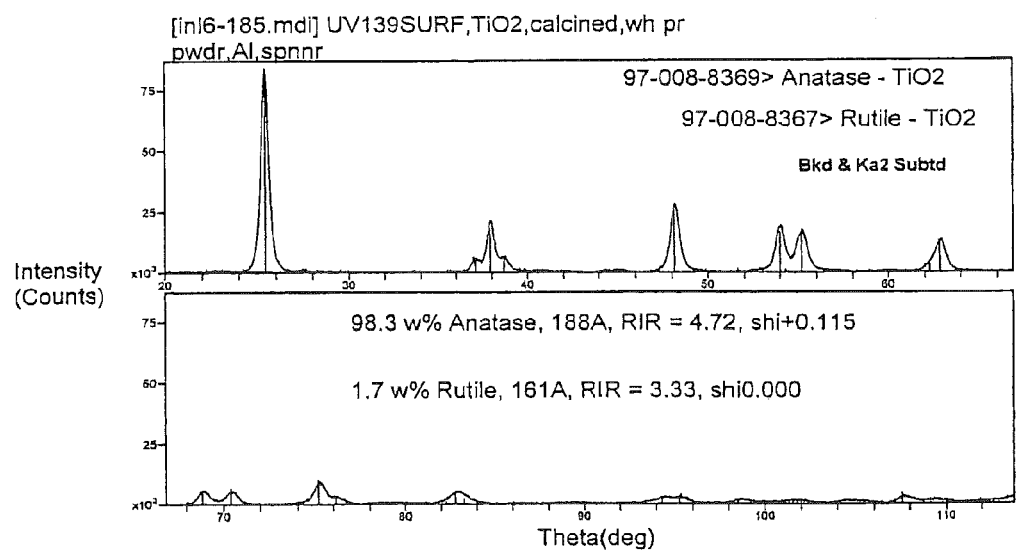
FIG. 6 illustrates a powder X-ray diffraction pattern of a photocatalyst that is outside the scope of the present disclosure, UV139, having anatase crystallites of 188 Angstroms (19 nm).

By comparison, FIG. 6 illustrates the x-ray diffraction pattern of a photocatalyst that is too large in size to be within the scope of the present disclosure, UV 139, which is predominantly anatase and has crystallites of about 19 nm (188 Angstroms) in diameter. As shown by the data in Table 2, above, UV139 has a larger deactivation rate from contaminants as compared with UV114.

Example 2

Figure 7:
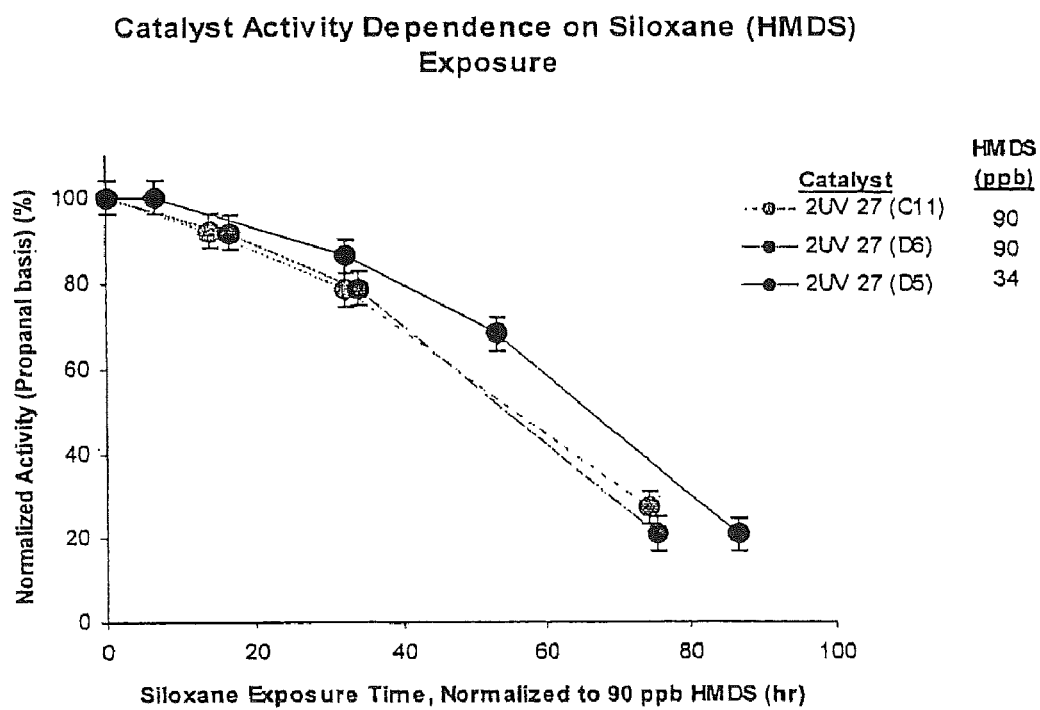
FIG. 7 illustrates effects of hexamethyldisiloxane concentrations on the deactivation rate of siloxane-resistant catalyst 2UV27.

FIG. 7 illustrates the results of an experiment showing the effect of various hexamethyldisiloxane concentrations on the deactivation rate of a siloxane-resistant catalyst, 2UV27. The abscissa, siloxane exposure time, was normalized to a selected hexamethyldisiloxane level (90 ppb). The linear scaling factor was equal to the exposure time multiplied by the hexamethyldisiloxane concentration divided by 90. Each catalyst was exposed to a controlled level of hexamethyldisiloxane for various periods of time. Periodically, the photocatalytic activity, and hence the rate of deactivation, was determined at various times, using propanal as the probe gas.

As shown in FIG. 7, the further a data curve trends to the right, the lower the deactivation rate of the photocatalyst. As the rate of deactivation of the photocatalyst decreases, this will correspond to a longer photocatalyst life. As shown by the data curves for 34 ppb hexamethyldisiloxane and 90 ppb hexamethyldisiloxane, the relationship between photocatalyst life and hexamethyldisiloxane concentration is non-linear. A lower concentration of hexamethyldisiloxane thereby results in a progressively longer catalyst life.

For example, in the particular instance of a deactivation level corresponding to the 50% loss in propanal activity, when the hexamethyldisiloxane level was decreased from 90 ppb to 34 ppb, the photocatalyst life increased by a factor of about 1.2 (ratio of normalized exposure time) over the linear increase corresponding to the ratio of hexamethyldisiloxane concentration (i.e., 2.65 equals 90 divided by 34), for a net increase in life of 3.18 times (i.e., 1.2×2.65). The inference from such data is that lowering the hexamethyldisiloxane concentration, as by using an adsorbent filter, for example, would result in a non-linear increase in photocatalyst life.

Example 3

Figure 8:
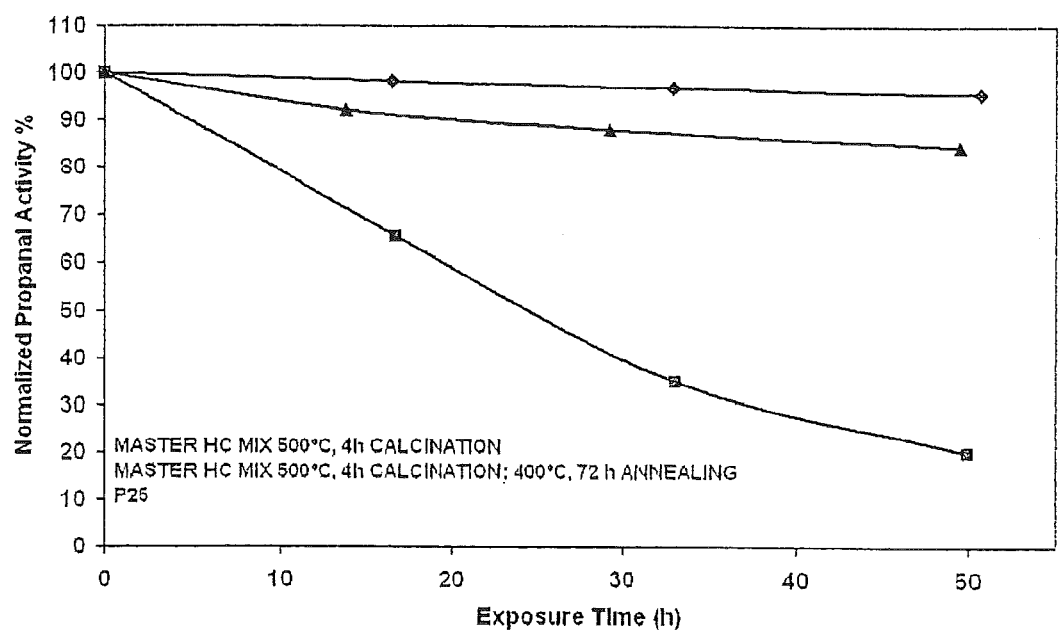
FIG. 8 is a graph illustrating the deactivation rates of two calcined $TiO_2$ photocatalysts of the present disclosure as compared with deactivation rates of commercially-available P25.

Several individual batches of high surface area, large cylindrical pore anatase-$TiO_2$ were prepared with $SnF_2$ additive, blended together and calcined in air at 500° C. for four hours. This was designated as the "Master Mix." One portion of this calcined Master Mix was cooled, slurried, and applied to an aluminum slide, dried, and tested for activity and activation life in the same manner as described in Example 1. The average deactivation rate of the calcined Master Mix, after 50 hours of testing, was 0.32% of Initial Single Pass Efficiency/hour (% ISPE/hr). A second portion of this Master Mix was returned to the furnace and annealed for 72 hours at 400° C. in air. The average deactivation rate for the calcined and annealed Master Mix, after 50 hours of testing, was 0.08% (% ISPE/hr), a clear improvement in performance, as shown by the data in FIG. 8. By comparison, the P25 DEGUSSA reference catalyst had a deactivation rate of 1.6% ISPE at the corresponding 50-hour point. Under these conditions, the new catalyst showed about a 2000% improvement in active life as compared with P25.

While the present disclosure has been described with reference to one or more exemplary embodiments, it will be understood by those skilled in the art that various changes may be made and equivalents may be substituted for elements thereof without departing from the scope of the present disclosure.

The invention claimed is:

1. A photocatalyst comprising nanocrystallites of titanium dioxide ($TiO_2$) that are less than 14 nanometers (nm) in diameter and that form one or more pores, wherein the $TiO_2$ nanocrystallites have at least 200 $m^2$ surface area/$cm^3$ of skeletal volume in pores with a diameter of 6 nm or larger, and wherein the mode of the pore size distribution is 10 nm or larger.

2. The photocatalyst according to claim 1, wherein the nanocrystallites of $TiO_2$ are substantially defect-free in order to maintain the semiconducting properties of $TiO_2$ and maintain electron hole separation for photocatalysis.

3. The photocatalyst according to claim 1, wherein the nanocrystallites of $TiO_2$ are less than 12 nm in diameter.

4. The photocatalyst according to claim 3, wherein the nanocrystallites of $TiO_2$ form pores that are cylindrical.

5. The photocatalyst according to claim 4, wherein the nanocrystallites of $TiO_2$ form porous particles of less than 1 micron.

6. The photocatalyst according to claim 1, wherein the nanocrystallites of $TiO_2$ further comprise a coating or layer of a dopant material selected from the group of metal, metal oxide, non-metal, and any combinations thereof.

7. The photocatalyst according to claim 6, wherein the dopant material is combined with the nanocrystallites of $TiO_2$ in the ratio of $Ti_{(1-x)}M_xO_2$ where Ti is titanium, x is mole fraction less than 0.1 and M is the doping material.

8. The photocatalyst according to claim 6, wherein the dopant material comprises a metal selected form the group consisting of tin, iron, zinc, niobium, tungsten, neodymium, cerium, molybdenum, hafnium, and any combinations thereof.

9. The photocatalyst according to claim 6, wherein the dopant material comprises a non-metal that is nitrogen.

10. The photocatalyst according to claim 1, wherein the nanocrystallites of $TiO_2$ form porous particles having a pore size that is the same size or larger than the size of the nanocrystallites of $TiO_2$.

11. A purification system for air, water, or fluids, comprising photocatalytic $TiO_2$ nanocrystallites that form porous particles, wherein said $TiO_2$ nanocrystallites are less than 14 nm in diameter.

12. A process of preparing nanocrystalline $TiO_2$ photocatalysts that are substantially free of internal defects comprising:
calcining nanocrystalline $TiO_2$ photocatalysts at a temperature of at least 200° C.,
wherein the calcining process is conducted in an oxygen-containing atmosphere that is free of silicon.

13. The process according to claim 12, wherein the nanocrystalline $TiO_2$ photocatalysts are calcined for 24 to 72 hours.

14. The process according to claim 13, wherein the nanocrystalline $TiO_2$ photocatalysts are calcined at a temperature from about 350° C. to about 450° C. for the majority of the calcining time.

15. The process according to claim 12, wherein the nanocrystalline $TiO_2$ photocatalysts are calcined at a temperatures from about 450° C. to about 550° C. from about 3 hours to about 5 hours.

16. The process according to claim 15, further comprising annealing the nanocrystalline $TiO_2$ photocatalysts at a temperature from about 350° C. to about 450° C. for an additional time from about 24 hours to about 72 hours, after calcining.

* * * * *